United States Patent [19]
Ruggiero et al.

[11] Patent Number: 5,814,661
[45] Date of Patent: Sep. 29, 1998

[54] USE OF PHTHALIDYLIDEN ESTERS OF CARNITINE AND ALKANOYL CARNITINES FOR THE TREATMENT OF ENDOTOXIC SHOCK

[75] Inventors: Vito Ulderico Ruggiero; Piero Foresta, both of Rome, Italy

[73] Assignee: Sigma-Tau Industrie Farmaceutiche Riunite S.p.A., Rome, Italy

[21] Appl. No.: 530,581

[22] Filed: Sep. 19, 1995

[30] Foreign Application Priority Data

Sep. 29, 1994 [IT] Italy .................................. RM94A0625

[51] Int. Cl.⁶ ..................................................... A61K 31/34
[52] U.S. Cl. ........................... 514/470; 514/468; 514/921
[58] Field of Search ..................... 514/470, 921, 514/468

[56] References Cited

U.S. PATENT DOCUMENTS 4,582,824   4/1986   Nishikawa et al. ....................... 514/77

OTHER PUBLICATIONS

Vito Ruggiero et al. "LPS–Induced Serum TNF Production and Lethality in Mice: Effect of L–Carnitine and Some Acyl–Derivatives". *Mediators of Inflammation*, vol. 2(Supplement), pp. S43–S50. 1993.

CAPLUS Abstract 1994:290039 (1993) Ruggiero et al.

*Primary Examiner*—Theodore J. Criares
*Assistant Examiner*—M. Moezie
*Attorney, Agent, or Firm*—Oblon, Spivak, McClelland, Maier & Neustadt, P.C.

[57] ABSTRACT

A therapeutical method for treating endotoxic shock which comprises administering to a patient in need thereof a (3-phthalidyliden) alkyl ester of carnitine or alkanoyl carnitine, is disclosed.

12 Claims, 2 Drawing Sheets

Figure 1   Effect of ST 899 treatment on lethality induced by LPS challenge, 30 mg/Kg i.p. (days 0). The treatment was performed by administering to mice (9 animals/group) ST 899, 5 mg/kg, 60 min. (i.p.) and 10 min. (i.v.) before the LPS challenge.
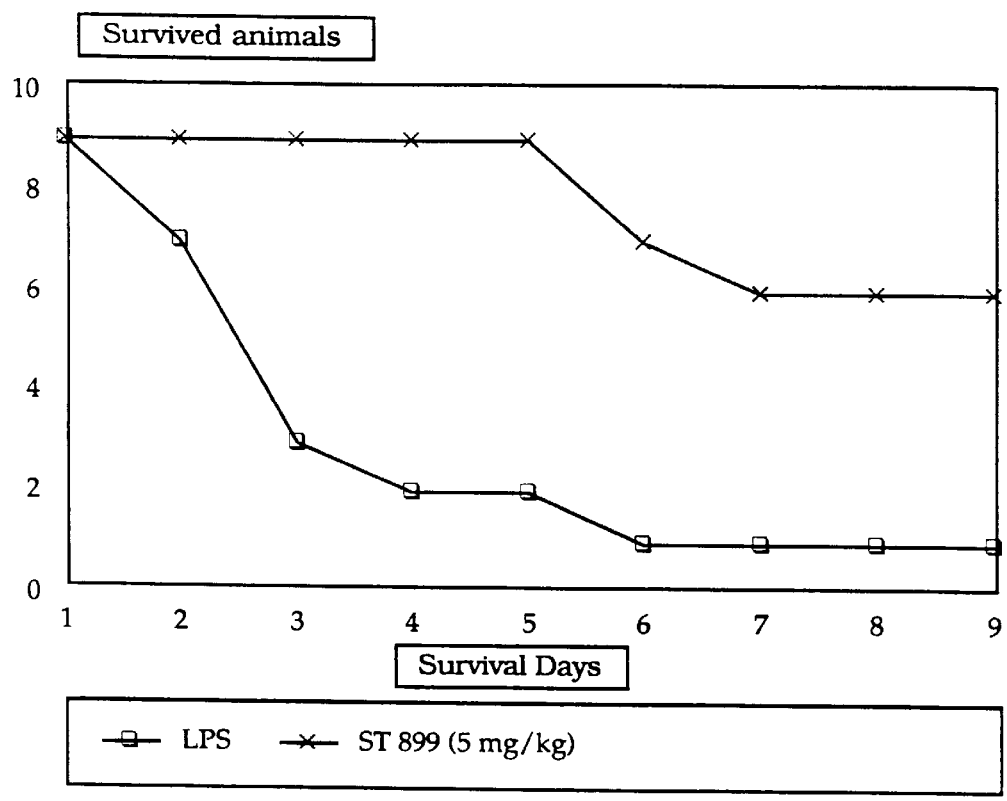

Figure 2  Effect of ST 899 treatment on lethality induced by LPS challenge, 30 mg/kg i.p. (day 0). The treatment was performed by administering to mice (10 animals/group) ST 899, 5 mg/kg, 60 min. (i.p.) and 10 min. (i.v.) before the LPS challenge.
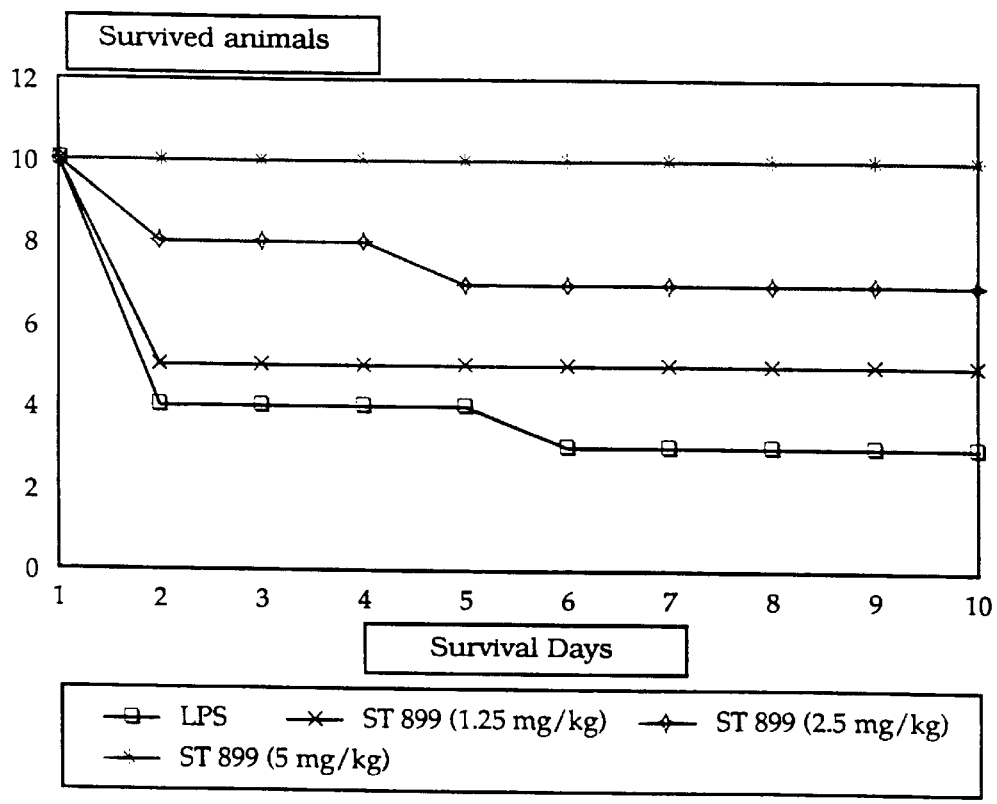

USE OF PHTHALIDYLIDEN ESTERS OF CARNITINE AND ALKANOYL CARNITINES FOR THE TREATMENT OF ENDOTOXIC SHOCK

The present invention relates to the use of (3-phthalidyliden) alkyl esters of carnitine and alkanoyl carnitines for preparing pharmaceutical compositions suitable for treating endotoxic shock.

These esters have the formula (I)

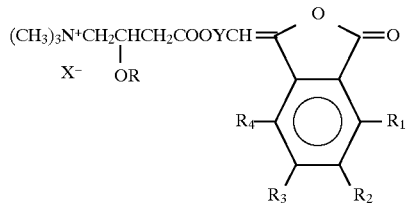

wherein
Y is a $C_1$–$C_5$ alkylene group, unsubstituted or substituted with one or more lower $C_1$–$C_4$ alkyl groups;
R is hydrogen or $C_2$–$C_6$ alkanoyl;
$R_1$, $R_2$, $R_3$ and $R_4$, identical or different, are hydrogen, halogen, $C_1$–$C_8$ alkoxy, lower $C_1$–$C_4$ alkyl, halogen-substituted lower alky, amino, alkyl-substituted amino wherein the alkyl group has 1 to 4 carbon atoms, nitro, cyano, $C_1$–$C_4$ alkanoylamino, or $R_1$ and $R_2$ taken together, $R_2$ and $R_3$ taken together or $R_3$ and $R_4$ taken together form a $C_1$–$C_4$ alkylenedioxy group, and
X is the anion of a pharmacologically acceptable acid.

In particular, in formula (I) the various substituents can have the following meanings:
Y is $C_1$–$C_4$ alkylene;
R is selected from hydrogen, acetyl, propionyl, butyryl, isobutyryl, valeryl and isovaleryl;
$R_1$, $R_2$, $R_3$ and $R_4$, identical or different, are selected from hydrogen, fluorine, chlorine, methoxy, ethoxy, methyl, trifluoromethyl, trichloromethyl, amino, nitro, cyano and acetylamino;
X is the anion of a pharmacologically acceptable acid selected from chloride; bromide; iodide; aspartate, particularly acid aspartate; citrate, particularly acid citrate; phosphate, particularly acid phosphate; fumarate, particularly acid fumarate; glycerophosphate; glucosephosphate; lactate; maleate, particularly acid maleate; orotate; oxalate, particularly acid oxalate; sulphate, particularly acid sulphate; trichloroacetate, trifluoroacetate and methanesulphonate.

According to the present invention, the following phthalidyliden derivatives are particularly preferred:

(Z)-[3-(5-chlorophthalidyliden) ethyl] ester of isovaleryl L-carnitine bromide (ST 899);
(Z)-(3-phthalidyliden) ethyl ester of isovaleryl L-carnitine bromide (ST 776);
(Z)-[3-(6-methoxyphthalidyliden) ethyl] ester of isovaleryl L-carnitine bromide (ST 867);
(Z)-[3-(6-fluorophthalidyliden) ethyl] ester of isovaleryl L-carnitine bromide (ST 900);
(Z)-[3-(6-fluorophthalidyliden) ethyl] ester of propionyl L-carnitine bromide (ST 926);
(Z)-[3-(7-chlorophthalidyliden) ethyl] ester of propionyl L-carnitine bromide (ST 954); and
(Z)-[3-(6-methylphthalidyliden) ethyl] ester of propionyl L-carnitine bromide (ST 1063).

The esters of formula (I) are known compounds; see, for instance, EP-A-0488965 where they were described as potent PAF (platelet-activating factor) and acetylcholinesterase antagonists and, consequently, useful as active ingredients in pharmaceutical compositions for treating those pathogical conditions wherein PAF is the etiological agent or one of the etiological agents. Furthemore, on the ground of their antagonism toward acetylcholinesterase, the esters of formula (I) have been described as active in the treatment of pre-senile and senile dementia (typically, Alzheimer disease). EP-A-0488965 which is incorporated herein by reference, discloses the physico-chemical characteristics and the preparation processes of the compounds (I).

It has now been found that the esters of formula (I) are active in counteracting endotoxic shock. This activity could not be foreseen on the ground of the already known pharmacological properties exibited by these compounds.

Endotoxic shock is a clinical syndrome associated with a high mortality rate and characterized by various haemodynamic, immunological and biochemical abnormalities.

Its increasing incidence places it among the most serious nosocomial pathologies, especially in intensive care units, despite the use of a variety of antibiotics, surgical drainage, intervention with vasoactive substances and metabolic support. It is estimated that approximately 100,000 people die of endotoxic shock every year in the USA.

The main cause of this type of pathology is undoudtedly severe infection with Gram-negative bacteria, whose physio-pathological effects are ascribable to LPS, a component of the outer layer of the bacterial membrane capable of causing endotoxic shock by interacting with various components of the host's immune system, particularly macrophages.

This immunocompetent cell population, in fact, releases different endogenous mediators which prove ultimately responsible for the complex pathological picture which ensues.

The fatal outcome of endotoxic shock in man has recently been linked to the systemic release of substantial amounts of various cytokines.

There are, in fact, numerous studies which show that an abnormal modulation of cytokines such as IL-1, IL-6, TNF and IFN-γ is closely related to a severe endotoxic situation.

Other inflammation mediators (PAF, LTD, BK, substances P) would also appear to be involved in the endotoxic pathophysiology.

TNF (Tumor Necrosis Factor) is, in any case, the cytokine which plays a crucial role as mediator in the host's response to LPS (Tracery K J, Tumor Necrosis Factor (Cachectin) in the Biology of Endotoxic Shock Syndrome. *Circ. Shock* 1991; 35: 123–128), since its involvement has been demonstrated in various metabolic abnormalities characterizing the course of shock (Starnes H K, Warren R S, Jeevandam M. et al. Tumor Necrosis Factor and the acute metabolic response to tissue injury in man. *J. Clin. Invest.* 1988; 82: 1321), the negative prognosis of which is often related to excessively high serum concentrations of TNF (Dames P., Reuter A., Gysen P., Demonty J., Lamy M., Franchimont P., Tumor Necrosis Factor and interleukin-1 serum levels during severe sepsis in humans. *Crit. Care Med.* 1989; 17: 975–978. Debets JMH, Kampmeijer R., Van Der Linden MPMH, Buurman W A, Vand Der Linden C J. Plasma Tumor Necrosis Factor and mortality in critically ill septic patients. *Crit. Care Med.* 1989; 17: 489–494).

In fact, high levels of TNF are found in the serum of animals experimentally intoxicated with LPS, and animals directely inoculated with TNF develop a toxic syndrome which is indistinguishable from endotoxinaemia (Natanson C., Eichenhols P W., Danner R L., Endotoxin and Tumor Necrosis Factor challenges in dogs simulate the cardiovascular profile of human endotoxic shock. *J. Ex. Med.* 1989; 169: 823–832. Beutler B., Milsak I W., Cerami A. Passive immunization against cachectin/Tumor Necrosis Factor protects mice from lethal effect of endotoxin. *Science* 1985; 229: 869–871).

Consequently, compounds which block or antagonize TNF may be regarded as useful therapeutical candidates in the treatment of endotoxic shock.

It was found that the esters having the formula (I) are endowed with such pharmacological properties.

BRIEF DESCRIPTION OF THE DRAWINGS

FIG. 1 and FIG. 2 are graphs showing the effect of ST 899 treatment on lethality induced by LPS challenge.
Assessment of the effect of (Z)-[3-(5-chlorophthalidylidene) ethyl] ester of isovaleryl L-carnitine bromide (ST 899) on TNF serum levels and LPS-Induced Lethality in C57BL/6 Mice Male C57BL/6 inbred mice (Iffa Credo) aged 7 weeks (8–10 animals per experimental group) were used.

ST 899, dissolved in sterile saline at 37° C., was administered following two distinct treatment protocols relative to the LPS challenge (30 mg/kg, at time 0), i.e.:

protocol A: at –60 min. per os and –10 min. i.v.;
protocol B: at –60 min. i.p. and –10 min i.v.

1.25 to 5 mg/kg doses were used which were selected based on studies of acute toxicity in mice.

Under the experimental conditions, the animals treated i.v. with the highest dose (5 mg/kg) exhibited reflex akinesia and intermittent convulsions from which they recovered five minutes following i.v. administration. No alterations were detected when the animals were treated with lower doses, i.e. 2.5 and 1.5 mg/kg, nor when the 5 mg/kg dose was administered orally or intraperitoneally.

055:B5 LPS extracted from *E. coli* dissolved in saline, was used.

TNF—Assay

Blood samplings were performed one hour following LPS administration, at which time TNF reached its peak levels. Blood samples were drawn from the retro-orbital plexus of the animals which had been previously anaesthetized via short $CO_2$-inhalation. Blood samples were incubated at room temperature for two hours and the serum thus obtained was centrifuged at 4,000 rpm for 20 minutes before being frozen at –80° C., preliminarily to serum TNF determination.

TNF activity was assayed by using L929 tumor cells (a murine fibrosarcoma) which have been shown to be especially sensitive to TNF cytotoxic activity.

In detail, L929 cells were seeded (cell density: $3,2 \times 10^5$ cells/mL) in the wells of a flat-bottomed microtiter plate (0.1 mL/well) using RPMI-1640 culture medium containing 10% FCS. Following incubation at 37° C. for 18–24 hours in a 5% $CO_2$-humidified thermostat, spent medium was discarded and 0.1 mL of serial dilutions (carried out in RPMI containing 1% FCS) of serum samples were added in triplicate to the wells.

Volumes of 0.1 mL of a 2 $\mu$g/mL solution of Actinomycin D were then added to each well. Actinomycin D inhibits RNA biosyntesis and, consequently, enhances L929 sensitivity to TNF cytotoxic activity.

After 18-hours incubation at 37° C. in a thermostat humidified with 5% $CO_2$, the supernatant was removed by suction and the cell monolayers washed three times with saline. The cells which adhered to the well bottoms were stained for 15 minutes with a Crystal violet solution (0.25% Crystal violet, 20% ethanol, 8% formaldehyde and $H_2O$ balance to 100 [w/v]).

The dye was removed by suction and the cells were gently washed with tap water. After the microtiter wells had been allowed to dry completely, the dye taken up by the cells was eluted with a 33% acetic acid solution and the sample absorbance measured at 570 nm with a microtite plate spectrophotometer (Multiskan MCC 340).

The absorbance values thus obtained were then utilized to determine the TNF activity (expressed in Units/ml) of each serum sample by directly comparing the regression curve generated by the serial dilutions of the various samples with the regression curve generated by the serial dilutions of a murine recombinant TNF standard of known activity.

Statistical Analysis

The statistical significance of the TNF results was evaluated by the Student "t" test. Survival data were analyzed by the Fischer exact test.

RESULTS

Effect of ST 899 on Serum TNF Release Induced by LPS

The results obtained by administering 5 mg/kg ST 899 according to protocols A and B are shown in table 1. It can be noticed that ST 899 significantly decreases LPS-induced circulating TNF.

A further experiment performed by administering ST 899 according to protocol B has shown that a serum TNF decrease of the same magnitude as above can be obtained also when lower ST 899 doses are used. Indeed, besides the significant decrease ($p<0.001$) obtained with 5 mg/kg, a significant lowering ($p<0.001$) of circulating TNF corresponding to 76% and 86% of LPS control was observed at the doses of 1.25 and 2.5 mg/kg, respectively. (see Table 2).

Effect of ST 899 on LPS-Induced Lethality

The results of a first experiment aimed at evaluating the effects of the ST 899 treatment on LPS-induced lethality are shown in Table 3.

In this case, the treatment with ST 899 (5 mg/kg) was conducted according to protocol B, i.e. by administering the compounds 60 min. (i.p.) and 10 min. (i.v.) before LPS challenge (30 mg/kg).

It can be noticed that, at the doses shown and following the aforesaid administration schedule, ST 899 is able to protect mice from LPS-induced lethality. Indeed, the survival of ST 899 treated animals significantly increases ($p<0.02$), reaching the peak of 66% (LPS control: 11%).

Also MST is significantly prolonged by ST 899 ($p<0.002$) (see Table 3 and FIG. 1) reaching the mean value of 11, markedly higher than that of LPS (MST=3 days).

Some protection expressed as both survival and MST, though not statistically significant, (see Table 4 and FIG. 2) can also be found when the animals are treated with lower ST 899 doses, i.e. 1.25 and 2.5 mg/kg.

Furthermore, it can be noticed from Table 4 that, in confirmation of the previous experiment reported in Table 3, the treatment with 5 mg/kg ST 899 proves again to be protective since both survival and MST increase significantly ($p<0.001$ and $p<0.02$, respectively).

The aforesaid tests show that ST 899, even at a dose as low as 1.25 mg/kg, is endowed with remarkable activity in inhibiting the formation of LPS-induced TNF.

In order to obtain significant effects on animal survival it is necessary, however, to administer a higher dose (5 mg/kg). This result purports that in our experimental model, in addition to TNF, other mediators participate as effectors in the cascade of events leading to the endotoxin-induced lethality.

TABLE 1

Effect of ST 899 administration on TNF serum levels (U/mL) induced by LPS challenge (30 mg/Kg i.p.).

| Animals | LPS | ST 899[a] | ST 899[b] |
|---|---|---|---|
| 1 | 660.72 | 104.94 | 279.28 |
| 2 | 214.06 | 141.92 | 154.30 |
| 3 | 1312.81 | 77.45 | 129.71 |
| 4 | 1391.02 | 197.15 | 81.80 |
| 5 | 731.78 | 104.94 | 206.42 |
| 6 | 319.30 | 147.67 | 143.93 |
| 7 | 632.91 | 108.64 | 111.70 |
| 8 | 781.62 | 79.34 | 103.34 |
| Mean | 755.53 | 120.26■ | 151.31▲ |
| S.E. | 147.79 | 14.17 | 22.62 |

[a]= ST 899 was administered at the dose of 5 mg/kg, 60 min. (i.p.) and 10 min. (i.v.) before LPS challenge.
[b]= ST 899 was administered at the dose of 5 mg/kg, 60 min. (per os) and 10 min. (i.v.) before LPS challenge.
Student "t" test: ▲= $p < 0.01$ and ■= $p < 0.001$.

TABLE 2

Effect of ST 899[a] administration on TNF serum levels (U/ml) induced by LPS challenge (30 mg/kg, i.p.).

| Animals | LPS | ST 899 (1.25 mg/kg) | ST 899 (2.5 mg/kg) | ST 899 (5 mg/kg) |
|---|---|---|---|---|
| 1 | 2452 | 209 | 215 | 160 |
| 2 | 308 | 169 | 156 | 75 |
| 3 | 1468 | 183 | 212 | 120 |
| 4 | 2232 | 127 | 135 | 77 |
| 5 | 969 | 505 | 233 | 211 |
| 6 | 606 | 227 | 149 | 95 |
| 7 | 1002 | 576 | 83 | 127 |
| 8 | 984 | 382 | 143 | 156 |
| Mean | 1252.63 | 297.25▲ | 165.75▲ | 127.63■ |
| S.E. | 266.25 | 59.65 | 17.82 | 16.51 |

[a]= The compound was administered at the doses shown 60 min. (i.p.) and 10 min. (i.v.) before LPS challenge.
Student "t" test: ▲= $p < 0.01$ and ■= $p < 0.001$.

TABLE 3

ST 899 protective effect assessed via a murine model of endotoxic shock. Survival variation and MST.

| Compound | Dose (mg/kg) | Survival S/T (%) | P[a] | MST[b] (days) | P[c] |
|---|---|---|---|---|---|
| LPS | 30 | 1/9 (11) |  | 3 (2.5–5) |  |
| ST 899 | 5[d] | 6/9 (66) | <0.02 | 11 (6.5–11) | <0.002 |

[a]= Fisher exact test.
[b]= Mean survival time, the interquartile ranges are reported in brackets.
[c]= Mann-Whitney "U" test.
[d]= ST 899 was administered 60 min. (i.p.) and 10 min. (i.v.) before LPS challenge (30 mg/kg i.p.).

TABLE 4

ST 899 protective effect assessed via a murine model of endotoxic shock. Survival variation and MST.

| Compound | Dose (mg/kg) | Survival S/T (%) | P[a] | MST[b] (days) | P[c] |
|---|---|---|---|---|---|
| LPS | 30 | 3/10 (30) |  | 2 (2–11) |  |
| ST 899 | 1.25[d] | 5/10 (50) | n.s. | 6.5 (2–11) | n.s. |
| ST 899 | 2.5[d] | 7/10 (70) | n.s. | 11 (4.25–11) | n.s. |
| ST 899 | 5[d] | 10/10 (100) | <0.001 | 11 (11–11) | <0.02 |

[a]= Fisher exact test.
[b]= Mean survival time, the interquartile ranges are reported in brackets.
[c]= Mann-Whitney "U" test.
[d]= ST 899 was administered 60 min. (i.p.) and 10 min. (i.v.) before LPS challenge (30 mg/kg i.p.).

Assessment of ST 899 Effects On LPS-Induced Lethality in C57BL/6 Mice Following D-galactosamine Sensitization Male C57BL/6 inbred mice (Iffa Credo) aged 6–8 weeks were used. ST 899, dissolved in sterile saline at 37° C., was administered following the treatment protocol outlined in Table 5.

The lipopolysaccharide (LPS) used is derived from *E. coli* and is the 055:B5 serotype.

055:B5 LPS was administered (0.01 mg/kg, i.p.) to mice which 30 min. before challenge had been treated with the sensitizing agent D-galactosamine (lg/kg, i.v.).

ST 899 Effect on 055:B5 LPS-Induced Lethality in Mice Following D-galactosamine Sensitization The data relating to ST 899 effects on D-galactosamine+ 055:B5 LPS-induced lethality in C57BL/6 mice are shown in Table 5.

As already known as regard this D-galactosamine/LPS model (see Galanos C., Freudenberg M. Immunobiol. 1993; 187: 346–356), in D-galactosamine pretreated mice the lethal effects of LPS were markedly enhanced.

According to this model, ST 899 administered i.p. 120, 60 and 10 minutes before LPS challenge was shown to be ineffective at the dose of 1.5 mg/kg. On the other hand, the administration of 15 mg/kg ST 899 was shown to be significantly effective (p<0.05) in protecting mice from LPS elicited lethality.

TABLE 5

Effect of ST 899 treatment in the D-galactosamine + 055:B5LPS model, in C57BL/6 mice. D-galactosamine (1 g/Kg) was administered i.v. 30 min. before LPS challenge (0.01 mg/kg, i.p.). The treatment with 1.5 and 15 mg/kg ST 899 was performed e.p. 120, 60 and 10 minutes before LPS challenge.

| DOSE (mg/kg) | TREATMENT | LETHALITY D/T[a] |
|---|---|---|
| 1.5 | −2 hours, −1 hour, −10 min. i.p. | 8/8 (7/8) |
| 15 | −2 hours, −1 hour, −10 min. i.p. | 2/8 (7/8)* |

[a]= Dead/Total: lethality of LPS control is shown in brackets.
[b]= $p < 0.05$ (Two-tailed Fisher test).

The compounds of the present invention are administered orally or parenterally in any of the usual pharmaceutical forms which are prepared by conventional procedures with which experts in these techniques are fully conversant. These forms include both solid and liquid oral unitary dosage forms such as tablets, capsules, solutions, syrups and the like, and injectable forms such as, for example, sterile solutions for vials and ampoules.

For these pharmaceutical forms the usual solvents, diluents and excipients are used. Optionally, preservative, sweetening and flavouring agents can be added. Non-exclusive examples of such substances are sodium carboxymethylcellulose, polysorbate, mannitol, sorbitol, starch, avicel, talc and others which are evident to experts in pharmacy.

The dose administered will be decided by the primary care physician, bearing in mind the patient's age, body weight and general condition, on the basis of an appropriate professional assessment.

Though effective results can be noted even at daily doses of from 5 to 8 mg/kg body weight, doses ranging from 10 to 50 mg/kg body weight are optimal. When considered necessary, larger doses can be given, owing to the low toxicity of the compounds of the present invention.

The dosages envisaged, according to the pharmaceutical administration form, are, though not exclusively, the following:

| | |
|---|---|
| ampoules | from 5 to 500 mg |
| capsules | from 15 to 50 mg |
| tablets | from 15 to 500 mg |
| oral solutions | from 15 to 50 mg |

What is claimed is:

1. A therapeutical method for treating endotoxic shock which comprises administering to a patient in need thereof prior to the onset of endotoxic shock to reduce the amount of tumor necrosis factor (TNF) produced during a subsequent endotoxic shock episode a therapeutically effective amount of a (3-phthalidyliden) alkyl ester of carnitine or alkanoyl carnitine of general formula (I)

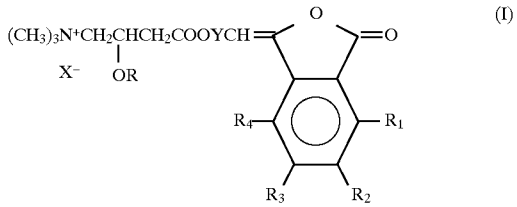

wherein:
  Y is a $C_1$–$C_5$ alkylene group, unsubstituted or substituted with one or more lower $C_1$–$C_4$ alkyl groups;
  R is hydrogen of $C_2$–$C_6$ alkanoyl; $R_1$, $R_2$, $R_3$ and $R_4$, identical or different, are hydrogen, halogen, $C_1$–$C_8$ alkoxy, lower $C_1$–$C_4$ alkyl, halogen-substituted lower alkyl, amino, alkyl-substituted amino wherein the alkyl group has 1 to 4 carbon atoms, nitro, cyano, $C_1$–$C_4$ alkanoylamino, or $R_1$ and $R_2$ taken together, $R_2$ and $R_3$ taken together or $R_3$ and $R_4$ taken together form a $C_1$–$C_4$ alkylenedioxy group, and X is the anion of a pharmacologically acceptable acid.

2. The method of claim 1, wherein Y is methylene or ethylene.

3. The method of claim 1, wherein R is selected from acetyl, propionyl, butyryl, isobutyryl, valeryl and isovaleryl.

4. The method of claim 1, wherein the ester of the formula (I) is (Z)-[3-(5-chlorophthalidyliden) ethyl] ester of isovaleryl L-carnitine bromide.

5. The method of claim 1, wherein the ester of the formula (I) is (Z)-(3-phthalidyliden) ethyl ester of isovaleryl L-carnitine bromide.

6. The method of claim 1, wherein the ester of the formula (I) is (Z)-[3-(6-methoxyphthalidyliden) ethyl] ester of isovaleryl L-carnitine bromide.

7. The method of claim 1, wherein the ester of the formula (I) is (Z)-[3-(6-fluorophthalidyliden) ethyl] ester of isovaleryl L-carnitine bromide.

8. The method of claim 1, wherein the ester of the formula (I) is (Z)-[3-(6-fluorophthalidyliden) ethyl] ester of propionyl L-carnitine bromide.

9. The method of claim 1, wherein the ester of the formula (I) is (Z)-[3-(7-chlorophthalidyliden) ethyl] ester of propionyl L-carnitine bromide.

10. The method of claim 1, wherein the ester of the formula (I) is (Z)-[3-(6-methylphthalidyliden) ethyl] ester of propionyl L-carnitine bromide.

11. The method of claim 1, wherein said amount administered to said patient is a daily dose of at least 5 mg/kg based on patient body weight.

12. The method of claim 1, wherein said (3-phthalidyliden) alkyl ester of carnitine or alkanoyl carnitine is administered in a pharmaceutical form selected from the group consisting of a tablet, capsule, solution, syrup and injection.

* * * * *